United States Patent [19]

Ford et al.

[11] Patent Number: 4,895,955

[45] Date of Patent: Jan. 23, 1990

[54] NON-RADIOACTIVE CARBODIIMIDE PRECURSOR TO NUCLEIC ACID PROBES

[75] Inventors: John P. Ford, Uradilla, N.Y.; Charles W. Blewett, Fort Mitchell, Ky.; Michael D. Sublett, Cincinnati, Ohio; Bernard F. Erlanger, Whitestone, N.Y.; Alan F. Cook, Cedar Grove, N.J.

[73] Assignees: Lifecodes Corporation, Valhalla; Quantum Chemical Corporation; Trustees of Columbia University, both of New York, all of N.Y.

[21] Appl. No.: 199,570

[22] Filed: May 27, 1988

[51] Int. Cl.$^4$ ............................................. C07D 495/04
[52] U.S. Cl. ........................................ 548/303; 435/6; 536/27
[58] Field of Search ......................................... 548/303

[56] References Cited

U.S. PATENT DOCUMENTS 4,751,313  6/1988  Levenson et al. .................. 548/303

Primary Examiner—Richard A. Schwartz
Attorney, Agent, or Firm—Pennie & Edmonds

[57] ABSTRACT

This invention relates to carbodiimide compounds of the formula:

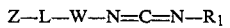

$$Z-L-W-N=C=N-R_1$$

wherein Z is a signalling moiety or a protecting group; L is a divalent linking group; W is an alkylene group having up to 24 carbon atoms which can be substituted or interrupted by a water solubility enhancing group or cleavable S—S group; and $R_1$ is an alkyl group having up to 18 carbon atoms. These compounds are useful in the nonradioactive labelling of nucleic acid probes, and methods employing same.

4 Claims, No Drawings

NON-RADIOACTIVE CARBODIIMIDE PRECURSOR TO NUCLEIC ACID PROBES

1. FIELD OF THE INVENTION

This invention relates to the field of nucleic acid detection by means of non-radioactive reagents. More specifically, the invention discloses a group of carbodiimide compounds that are particularly useful as components in a non-radioactive nucleic acid hybridization detection system.

2. BACKGROUND OF THE INVENTION

The technique of nucleic acid hybridization has been successfully employed for the study of DNA structure, nucleic acid purification, gene localization, and detection and diagnosis of diseases and mutations.

Hybridization assays are based on the structural properties of DNA molecules. The DNA of most organisms is comprised of two strands of polynucleotides which associate largely through noncovalent interactions into the familiar double helical structure. The most important of these noncovalent interactions is hydrogen bonding between adenine and thymine and between cytosine and guanine. It was demonstrated by Britten, et al. (*Sci. American* 222(4):24–31 (1968)) that under certain conditions it was possible to cause the two strands to separate from one another. This process of strand separation has been variously referred to as an unwinding, denaturing or melting of the double-stranded duplex. It was further discovered that under a second set of conditions the strands would reassociate to reform the duplex DNA structure, this process being referred to as annealing, reassociation or renaturation.

It is also now known to be possible to denature DNAs from two different sources, then mix the two populations of single stranded nucleic acids, and under renaturation conditions estimate the percentage of double stranded hybrids formed, thus providing an indication of sequence homology between the two sources. The double-stranded molecules formed are hybrids, and the process is known as DNA hybridization. In a similar manner, a small nucleotide segment ranging from a fraction of a single gene up to a size which would include several genes may be used to hybridize to DNA for the purposes of determining whether a complementary segment is present in the sample, and if so, where it is located. The segment of interest is often of a predetermined sequence or function and is generally referred to as a nucleic acid hybridization probe.

Such probes have become extremely important as reagents for the detection of specific nucleic acid sequences. Commonly the probes are labelled with radioactive isotopes to facilitate their analytical detection. The isotopes normally employed include $^{32}P$, $^{125}I$ or $^{3}H$; however, considerations regarding stability, safety, ease of detection and disposal of waste have fostered the development of non-isotopically labelled probe molecules.

One approach has been to detect nucleic acids by immunological means, either by developing antibodies which will discriminate between single and double stranded DNAs or by labelling the nucleic acid with an immunoreactive component such as a hapten. Landegent, et al. (*Exp. Cell Res.* 153:61–72 (1984)) and Tchen et al. (*Proc. Nat'l Acad. Sci. USA* 81:3466–3470 (1984)) have employed N-acetoxy-N-2-acetylaminofluorene to label probes. These probes can be detected by direct or indirect enzyme-linked immunosorbent assays (ELISA). Because of the carcinogenic nature and attendant disposal problems associated with N-acetoxy-N-2-acetylaminofluorene, alternative methods are desired.

A hapten which has gained widespread use for labeling nucleic acid molecules is the vitamin, biotin. Of particular advantage is the high affinity ($k_d = -^{15}M$) between biotin and the glycoprotein avidin (Green, N. M., *Adv. Protein Chem.* 29:85–133 (1975)). This affinity is stronger than that between a typical antibody and a typical antigen. Moreover, it was found that avidin could be reacted with enzymes, fluorescent groups or electron dense molecules to form analytically detectable avidin-conjugates.

Ward, et al. (*Proc. Nat'l Acad. Sci. USA* 79:4381–4385 (1982) and *Proc. Nat'l Acad Sci. USA* 80:4045–4049 (1983)) have developed a method for labeling nucleic acids with biotin. Biotin-labelled analogs of nucleic acid precursors such as dUTP and UTP were enzymatically incorporated into nucleic acids. The method of Ward et al. requires expensive substrates and enzyme, and large scale preparation of biotin labelled nucleic acids by this method is economically disadvantageous. It was desirable, therefore, to develop chemical methods for labelling nucleic acid with biotin.

Several attempts to develop chemical labelling methods have been reported. Manning et al. (*Chromosoma* 53:107–117 (1975)) have disclosed the chemical cross-linking of a biotin labelled cytochrome C conjugate to RNA with formaldehyde. M. Renz and C. Kurz substituted enzymes such as peroxidase or alkaline phosphatase for cytochrome C in a similar crosslinking procedure (*Nucleic Acid Res.* 12(8):3435–3444 (1984)). However, the conjugates tend to be unstable under hybridization conditions. Moreover, the adducts to the nucleic acid often present serious steric hindrance to the hybridization process.

Finally, Forster, et al. (*Nucleic Acid Res* 13(3):745–761 (1985)) have disclosed the synthesis of a photoactivatable biotin analog of the formula:

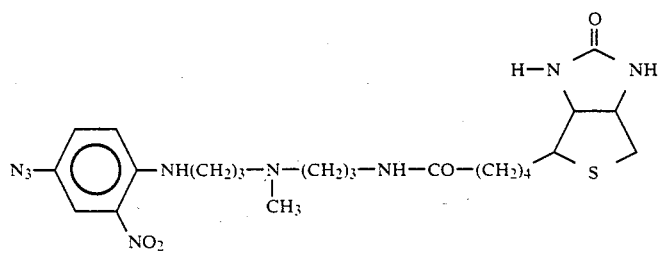

which may be used to label M13 DNA probes. However, this compound reacts with both single and double stranded DNA and as pointed out by the authors, this dual reactivity limits the extent of probe modification possible without interfering with the hybridization of target sequences by single stranded regions of the probe.

Carbodiimides have been previously reported to be useful for peptide synthesis (J. C. Sheehan et al., *J. Org. Chem.* 21:439 (1956)). The reactivity of carbodiimides with guanine and thymidine nucleotides has been reported by P. T. Gilham (*J. Am. Chem. Soc.* 84:688 (1962)).

3. BRIEF DESCRIPTION OF THE INVENTION

This invention relates to a carbodiimide compound of the formula:

$$Z-L-W-N-=C=N-R_1$$

wherein Z is a signalling moiety or protecting group; L is a divalent linking group; W is an alkylene group having up to 24 carbon atoms which can be substituted with or interrupted by a water solubility enhancing group or cleavable S—S group; $R_1$ is each alkyl or substituted alkyl of up to 18 carbon atoms. These compounds will hereinafter be referred to as compounds of Formula I.

Preferably, W is the group

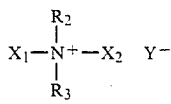

$$X_1-\overset{R_2}{\underset{R_3}{N^+}}-X_2 \quad Y^-$$

wherein $X_1$ and $X_2$ are each alkylene groups having from 1 to 18 carbon atoms, $R_2$ and $R_3$ are each alkyl groups having from 1 to 18 carbon atoms, and $Y^-$ is a counterbalancing anion.

In a preferred embodiment, the compounds have the formula:

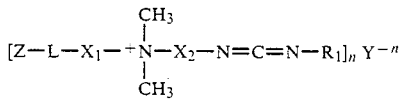

$$[Z-L-X_1-\overset{CH_3}{\underset{CH_3}{N}}-X_2-N=C=N-R_1]_n \ Y^{-n}$$

where Y is an anion, and n is an integer from 1–3. When Z is a signalling moiety, it is preferably chosen from a group consisting of biotin, a hapten, an antigen, an antibody, a photoreactive group, an enzyme, a fluorescent molecule, a chemiluminescent molecule, and a heavy-metal containing compound.

This invention also relates to a non-radioactively labelled nucleic acid probe comprising a single-stranded polynucleotide sequence complementary to the nucleic acid to be detected, said polynucleotide sequence having covalently attached thereto a carbodiimide-linked signalling moiety.

The invention also provides a method for preparing a polynucleotide probe comprising:

(i) providing a first polynucleotide sequence comprising a polynucleotide sequence of interest and a polynucleotide sequence not of interest, wherein (a) the polynucleotide sequence of interest is covalently linked to the polynucleotide not of interest; and (b) the polynucleotide sequence not of interest comprises at least one unpaired guanine, thymine or adenine base;

(ii) hybridizing the first polynucleotide sequence with a polynucleotide sequence complementary to the polynucleotide sequence of interest;

(iii) labelling the first polynucleotide sequence which has been hybridized with the polynucleotide sequence complementary to the polynucleotide sequence of interest with a carbodiimide-linked signalling moiety; and (iv) dissociating the polynucleotide sequence complementary to the polynucleotide sequence of interest from the first polynucleotide sequence under conditions for dissociation of polynucleotide duplexes.

The invention also provides a method for the detection of a target nucleic acid sequence comprising:

(i) hybridizing to the sequence to be detected a polynucleotide probe having covalently attached thereto a carbodiimide-linked signalling moiety to form a hybrid between the target sequence and the probe; and (ii) indicating the presence of the hybrid by detecting the signalling moiety, whereby the target sequence is detected.

The invention also provides a method for detecting duplex DNA containing single base mismatches comprising:

forming a duplex DNA molecule containing at least one single base mismatch;

reacting said mismatched duplex DNA with a compound of Formula I;

and identifying said reacted mismatch duplex DNA by detecting the Z group.

The invention provides a method for purifying perfectly matched heteroduplex DNA comprising (a) forming a mixture of perfectly matched and imperfectly matched heteroduplex DNA (b) reacting the mixture with a compound of Formula I; and (c) separating the labelled imperfectly matched heteroduplex DNA from the unlabelled perfectly matched heteroduplex DNA.

In a final embodiment the invention provides a method for preparing compounds of the formula

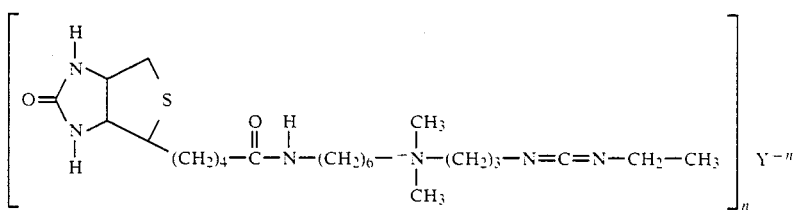

wherein Y and n have the meanings stated above comprising:

reacting biotin with isobutyl chloroformate and 6-amino-1-hexanol in the presence of N,N-dimethylformamide and tributylamine to form N-(6-hydroxyhexyl) biotinamide;

reacting said biotinamide with methyltriphenoxyphosphonium iodide in the presence of dimethylformamide to form N-(6-iodohexyl)biotinamide; and reacting said iodohexyl biotinamide with distilled 1-(3'-dimethylaminopropyl)-3-ethylcarbodiimide to yield the compound of the formula above.

4. DETAILED DESCRIPTION OF THE INVENTION

This invention provides a rapid, easily employed reagent for the chemical labelling of DNA with non-isotopic analytically detectable moieties. Reagents useful in practicing this invention are carbodiimide compounds which have been derivatized.

The derivative molecules can be conceptualized as consisting of three regions:

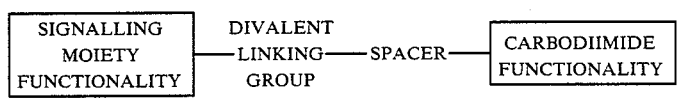

Carbodiimide compounds are particularly useful as reactive functionalities for DNA. Such compounds are known to react most strongly with unpaired guanine and thymine residues in DNA (P. T. Gilham, *J. Amer. Chem. Soc.* 84:688 (1962)). Although this reactivity is important as it provides a convenient means of derivatization of nucleic acids, to be useful as a component of a non-radioactive probe, the carbodiimide compound itself must include functionalities serving as signalling moieties.

Signalling moieties include, but are not limited to, biotin, haptens, antigens, antibodies, enzymes, chemiluminescent groups, a photoreactive group, fluorescent groups such as Texas Red, fluorescein, rhodamine, or phycoerythrins, and heavy metal-containing compounds such as ferritin. The signalling moieties should permit easy, reliable, and sensitive detection, should not interfere with the hybridization process, nor be chemically affected thereby, and should be assayable following hybridization under conditions in which the hybrid is maintained.

In another embodiment of the present invention, Z may be an amino-protecting group, such as carbobenzoxy, trichloroethoxycarbonyl, iodoethoxycarbonyl, trifluoroacetyl, chloroacetyl, or any other group which can be removed under relatively mild conditions. Although not strictly speaking a signalling moiety, carbodiimide compounds of the present invention in which Z is a protecting group may be utilized in introducing a signalling moiety onto a DNA molecule. Briefly, a temporary protecting group is introduced to a carbodiimide molecule. The carbodiimide reagent would then be used to introduce a functionalized linker arm onto DNA, first by reaction of the protected carbodiimide molecule with DNA, followed by removal of the protecting group, to yield a primary amino group, and, finally, linking of the signalling moiety to the primary amino group. For example, the carbobenzoxy group can be removed by treatment with hydrogen at atmospheric pressure in the presence of 10% palladium or carbon as catalyst. The trichloroethoxy carbonyl group can be removed by treatment with zinc dust, the trifluoroacetyl group can be removed with dilute ammonium hydroxide, and the chloroacetyl group with thiourea.

The signalling moiety is beneficially separated from the carbodiimide functionality by means of a molecular spacer. The spacer is preferably an alkylene group consisting of up to 18 carbon atoms in the principle chain and a total of up to 24 atoms and may be substituted with nonreactive solubility enhancing groups such as substituted and unsubstituted quaternary amines and/or cleavable —S—S-containing moieties. By non-reactive it is meant that substituents do not participate in the derivatization reaction under the conditions employed. In addition to the substituent not participating in the primary reactions, it is substantially incapable of forming undesirable secondary reactions.

The nature of L, the divalent linking group, will vary depending on the identity of Z and W. For example, L may be

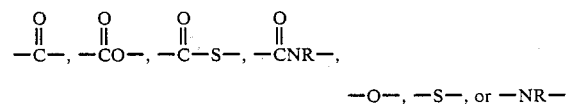

$$-O-, -S-, \text{ or } -NR-$$

wherein R is hydrogen or an alkyl group.

Certain of the carbodiimide compounds are conveniently prepared by the following route (DMF=N,N-dimethylformamide; $Bu_3N$=tributylamine; MeP-$(OC_6H_5)_3Y^-$=methyl triphenoxyphosphonium halide):

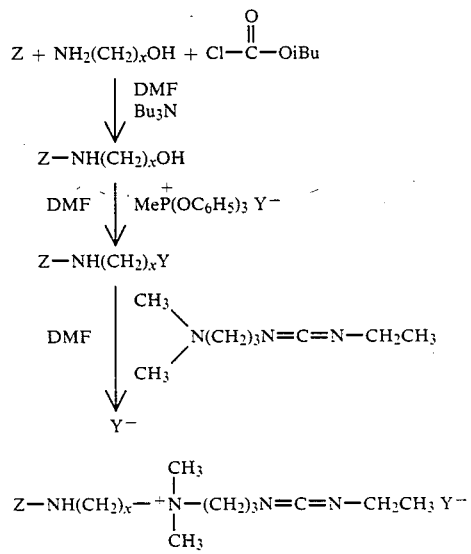

wherein x is an integer from 1-24 and the remaining substituents have the meanings as previously defined.

Generally, the carbodiimide compounds are formed as quaternary ammonium salts. The anion of these salts can be chloride, iodide, bromide, phosphate, metaphosphate, nitrate, and sulfate, as well as anions of organic acids such as tartaric, acetic, citric, malic, benzoic, glycolic, gluconic, succinic, arylsulfonic, e.g., p-toluenesulfonic acids, and the like. Accordingly, $Y^-$ is preferably $F^-$, $Cl^-$, $Br^-$, $I^-$, $HSO_4^-$ or

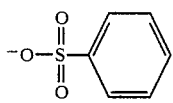

Of course, the stoichiometry is a function of the anions used, hence the number of carbodiimide molecules is, for example, 1 when $Cl^-$ is used, up to two when $H_2SO_4^{-2}$ is employed and up to 3 when phosphate is employed.

The details of the synthesis of some of these compounds are provided in Example 1.

CONSTRUCTION OF NON-RADIOACTIVE LABELLED PROBE

Non-radioactive probes useful for the detection of nucleic acids can be prepared according to the following procedure.

A polynucleotide sequence corresponding to a target sequence of interest is obtained from a natural source or by chemical or biochemical synthesis.

A portion of the target DNA sample is rendered single-stranded by denaturation and placed on a nitrocellulose filter. A second sample of the target DNA is incorporated in double stranded form into the RF form of a M13 cloning vector. The M13 vector containing the target sequence is introduced into a suitable *E. coli* host by transformation. A recombinant virus comprising the target DNA insert is selected and cultured in an *E. coli* host and its single stranded DNA is isolated from the virus particles. M13 vectors are commercially available and detailed instructions for the cloning of DNA by means of the vectors are provided by the manufacturer (see, e.g. M13 Cloning/Dideoxy Sequencing Instruction Manual, Bethesda, Res. Lab. Life Techn. Inc., Gaithersburg, Md. 20877).

A sample of the target DNA can be similarly cloned into a vector such as pSP64 (Promega Biotech, Madison, Wisc. 53711) from which a single-stranded RNA molecule complementary to only the target DNA can be isolated.

The single-stranded RNA is hybridized to the single-stranded close circular DNA to form a partially double-stranded molecule, where the M13 vector portion remains single-stranded. This molecule is exposed to the carbodiimide reagent, which reacts with unpaired thymine and guanine residues in the single-stranded region of the molecule. The unreacted reagent is washed away by ethanol precipitation of the derivatized nucleic acid. The RNA portion of the molecule is then removed by digestion with RNAase H using standard procedure. The resulting M13-probe is single-stranded over the target region and derivatized over the vector region.

Alternatively the M13-probe can be prepared in the following way:

This single-stranded DNA is hybridized to a complementary single stranded target molecule that had been previously attached to the nitrocellulose filter to form a complex which is partially double stranded and partially single stranded. A carbodiimide reagent is reacted with the complex to derivatize unpaired guanine, thymine, and adenine bases. Since the sequence immobilized on the nitrocellulose filter is totally complementary to the DNA insert of the recombinant viral DNA by design, the unpaired, derivatized bases are expected to be on the M13 vector sequence proper.

The unreacted reagent is washed from the filter and the carbodiimide-derivatized M13 recombirant molecule is eluted from the filter and may be used as a non-radioactive probe. Accordingly, a sample of DNA containing the target sequence is isolated, denatured and attached &to a nitrocellulose filter. The M13 probe reagent is added, and is bound to the filter by virtue of the hybridization reaction between the target sequence on the filter and its complement integrated Within the M-13 reagent. Unreacted probe is removed by extensive washing of the filters. The presence of the signalling moiety incorporated into the M13 probe through the above reactions is then indicated by reaction with the appropriate reagents, for example if the group is biotin, it may be detected by reaction with enzyme-conjugated avidin or streptavidin followed by addition f a color forming substrate of the enzyme and detection of the colored product formed. Alternatively, if the signalling moiety is a hapten or antigen, an antibody may be employed. This antibody may be conjugated directly to an enzyme and detected enzymatically as above, or the unconjugated antibody can be detected by a second anti-globulin that is enzymatically labelled.

If the analytically detectable group is a photoreactive group, fluorescent group or a heavy metal containing compound, they may be detected by the appropriate photoreaction, fluorescent or heavy metal detection technique.

The biotin-avidin or biotin-streptavidin detection system is preferred. In addition to the high affinity of avidin for biotin as mentioned above, avidin is tetrameric with respect to biotin and as such permits the formation of super molecular aggregates, thereby resulting in signal amplification.

5. PURIFICATION AND IDENTIFICATION OF DNA-CONTAINING SINGLE BASE MISMATCHES

In a further embodiment the carbodiimide compounds of this invention may be used to detect single base pair mismatches in DNA. If, after hybridization, the double stranded molecule contains a mispaired region of a single base pair or more in which a T or G base is unpaired, then reaction with the carbodiimide compound is possible. If the carbodiimide compound contains a biotin functionality, then an immobilized avidin support can be employed to capture the mismatched hybrids. If the immobilized avidin is used in a column, then a mixture of mismatch hybrids and perfectly matched DNA duplexes may be resolved. In this embodiment the mismatched sequences are reacted with a biotinylated carbodiimide compound (the perfectly matched duplexes are of course unreactive), the mixture is then poured through the avidin column and the biotinylated mismatch sequences are retained while the duplex DNA is washed through the matrix. As such this embodiment provides an improved method for gene purification. Of course if another analytically indicatable functionality is employed (e.g. antigen or hapten) then the column would be comprised of the appropriately immobilized antibody.

In yet a further embodiment the carbodiimide compound of this invention can be used to label mismatches after in situ hybridization experiments, where after the mismatches are labelled, the signalling moiety can be detected by reaction with ferritin labelled avidin or antibody and then visualized by electron microscopy.

EXAMPLE 1

This example describes the preparation and characterization of a biotinylated carbodiimide salt useful as a nucleic acid labelling reagent. The numbers in parentheses after compound names refer to formulas in the scheme at the end of the example.

1. N-(6-hydroxyhexyl)biotinamide (2)

A mixture of 10.0 g (41 mmoles) biotin (1) and 800 ml N,N-dimethylformamide was stirred until all of the biotin had dissolved. Then 12.8 ml (53.8 mmoles) of tributylamine was added and the solution stirred for 10 minutes. To this solution was added 6.4 ml (49.4 mmoles) of isobutyl chloroformate followed by stirring for 30 minutes. This solution was then slowly added to a cold ($-5°$ C.) solution of 5.80 g (49.4 mmoles) 6-amino-1-hexanol in 800 ml N,N-dimethylformamide. Addition took place over a 30-minute period, and the temperature of the reaction mixture was maintained at $0°$ C. during the addition. After addition was complete, the reaction mixture was stirred at $0°$ C. for 3 hours, then allowed to warm to $20°$ C. The solution was evaporated under high vacuum (2 Torr) and the residue was dissolved in 400 ml of anhydrous ethanol with heating. The solution was stored at $-20°$ C. overnight, filtered, and the white crystalline precipitate washed with anhydrous ethanol. The washed precipitate was allowed to air dry to yield 13.4 g of white crystals, with an Mp of $170°-176°$ C. Recrystallization from anhydrous ethanol yielded material of MP $179°-181°$ C.

Mass Spectrum: 343 (molecular ion), 283, 227, 266, 118, 97.

Infrared Spectrum: 3288 cm$-1$ (broad), 1699 cm$-1$, 1676 cm$-1$, 1637 cm$-1$, 1541 cm$-1$, 1060 cm$-1$.

$^1$H NMR Spectrum: Triplet, 3.54, J=6 Hz, methylene adjacent to hydroxyl; Triplet, 2.19, J=7 Hz, methylene adjacent to amide carbonyl.

$^{13}$C NMR Spectrum: 171.9, amide carbonyl; 162.8, ureido carbonyl; 59.2, methylene adjacent to hydroxyl group.

2. N-(6-iodohexyl)biotinamide (3)

A mixture of 3.43 g (10 mmoles) N-(6-hydroxyhexyl)biotinamide (2), 9.04 g (20 mmoles) methyltriphenoxyphosphonium iodide, and 100 ml dry dimethylformamide was stirred in the dark at $25°$ C. for 1 hour. Then 3.0 ml of methanol were added. The solution was stirred at $25°$ C. for 20 minutes and then evaporated to approximately ⅓ its original volume under vacuum. Ethyl ether was then slowly added with stirring until no additional oily material separated. After two hours of stirring, the oily material had solidified on the sides of the flask. The solvent was decanted and the residue recrystallized from ethanol. The yield of product was 4.18 g. MP $153°-157°$ C. Mass Spectrum: 453 (molecular ion), 436, 420, 409, 393, 326, 282, 265, 227, 166, 128 (HI), 127 (I), 100, 96.

Infrared Spectrum: 3305 cm$^{-1}$ (broad), 1708 cm$^{-1}$, 1642 cm$^{-1}$ 1547 cm$^{-1}$.

$^1$H NMR Spectrum: Triplet, 3.23, J=6 Hz, methylene adjacent to iodine; Triplet, 2.20, J=7 Hz, methylene adjacent to amide carbonyl.

3. 1-(3'-N-6-biotinamidylhexyl-N,N-dimethylaminopropyl)-3-ethylcarbodiimide Iodide (4)

A mixture of 10 g 1-(3'-dimethylaminopropyl)-3-ethyl carbodiimide hydrochloride, 210 ml methylene chloride, and ml 40% potassium carbonate solution was stirred rapidly at $25°$ C. for 10 minutes. The methylene chloride layer was separated, dried over magnesium sulfate, filtered, and evaporated to yield 8.11 g of residue. Treatment of the potassium carbonate layer with 210 ml of methylene chloride was repeated and 0.50 g of residue obtained after evaporation. The two residues were combined and distilled under vacuum to give 7.07 g of a colorless liquid, BP $62°$ C. @ 0.8 Torr, refractive index ($26°$ C.) 1.4587 in accordance with values reported in the literature for 1-(3'-dimethylaminopropyl)-3-ethylcarbodiimide. A solution of 1.255 g (2.77 mmoles) N-(6-iodohexyl)biotinamide (3) in 30 ml of dry dimethylformamide was prepared and to this solution was added 0.473 g (3.05 mmoles) of distilled 1-(3'-dimethylaminopropyl)-3-ethylcarbodiimide. The resultant solution was heated to $50°$ C. and then stirred overnight at $25°$ C. Diethl ether was added to the solution with stirring until no more precipitate formed. After 30 minutes settling, the oily material that remained was dissolved in anhydrous ethanol. Ether was then added to effect precipitation. The solvent was decanted and the residue dried under high vacuum to yield 1.34 g of a deliquescent yellow solid.

Infrared Spectrum: 3287 cm$^{-1}$ (broad), 2126 cm$^{-1}$ 1703 cm$^{-1}$, 1645 cm$^{-1}$, 1549 cm$^{-1}$. $^1$H NMR Spectrum: Singlet, 3.15, quaternary methyls. $^{13}$C NMR Spectrum: 175.9, amide carbonyl; 165.0, ureido carbonyl; 140.7, carbodiimide; 51.7, quaternary methyls.

The above synthetic route may be illustrated as follows:

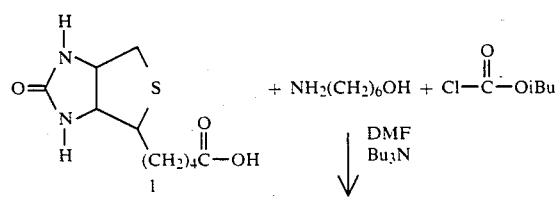

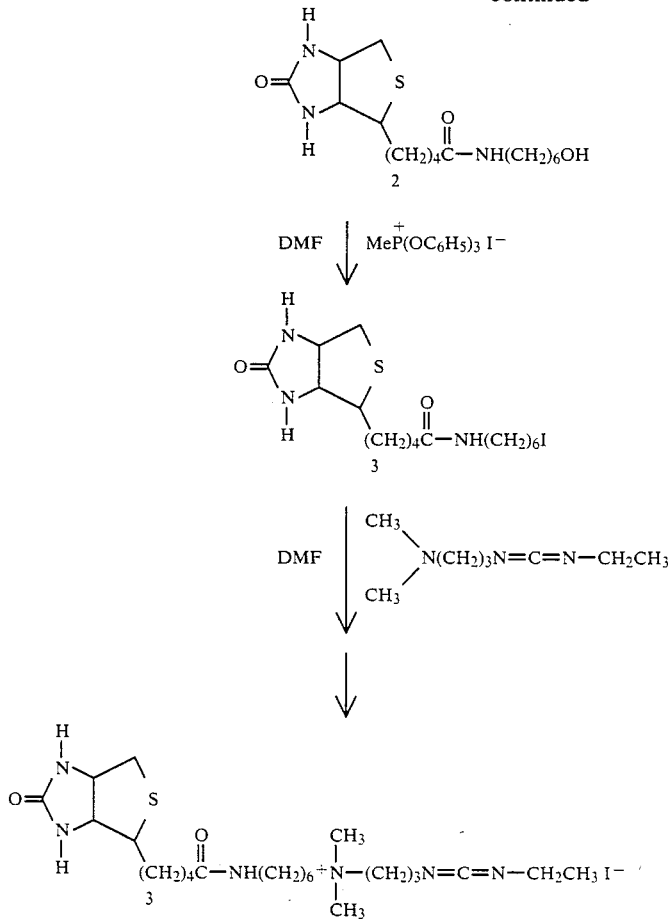

EXAMPLE 2

This example illustrates the stability of the carbodiimide compound of Example 1 under reaction conditions used to derivatize nucleic acids.

Stability of the carbodiimide (4), otherwise referred to as carbobiotin was measured by use of an aniline assay for carbodiimides (A. Williams, S. V. Hill, & I. T. Ibrahim, *Anal. Biochem.* 114:173–176, 1981). In brief, the assay was performed as follows: 15 µl of the sample to be measured was mixed with 15 µl of 1 M aniline hydrochloride. After at least one minute, 20 µl of the mixture was added to 1 ml of 1 M HCl. After at least 5 minutes, absorption was measured at 230 nm, and was compared to the absorption of a solution containing no carbobiotin. The sensitivity of this assay for carbobiotin ranges from about 0.5 mM to 20 mM in the original sample before dilution. Under conditions for reaction with single-stranded DNA, described infra, i.e., 100 mM carbobiotin, 30–100 mM borate, pH 8.5, only about 5% of the carbobiotin becomes unreactive (that is, combines with water) after 24 hours. Standard incubation times are well within this range.

EXAMPLE 3

This example demonstrates a time course for the reaction of the compound of Example 1 with single-stranded DNA.

The reaction of carbobiotin with single-stranded DNA was tested under two conditions: 100 mM borate and 30 mM borate, pH 8.5. At low ionic strength the carbobiotin reacts much more quickly with the DNA. The reaction of CB (carbobiotin) with DNA is measured by a) retardation of mobility on an agarose gel and b) reaction of the transferred DNA with streptavidin-peroxidase. As can be seen with reference to FIG. 1, maximum reaction and maximum recovery of CB-DNA are obtained at 8 hours reaction time; at the other extreme, a small amount of reaction occurs after just one hour.

Standard procedure for carbobiotin experiments:
(1) Carbobiotin reaction incubation conditions:
100 mM carbobiotin
30–100 mM borate, pH 8.5
0.1 µg/µl single-stranded M13 DNA
0.25% SDS
(2) After reaction, run on spin column to remove excess carbobiotin.
 (Sepharose CL/6B, buffer—⅓×Trisborate-EDTA buffer+0.25% SDS)
(3) Run on gel—1% agarose, 1×Tris-borate-EDTA buffer, +1 µg/ml ethidium bromide.
(4) Running conditions: 100 V, 2–4 hours.
(5) Transfer to nitrocellulose overnight.
(6) Bake 1 hour in 80° C. vacuum oven.
(7) Incubate with streptavidin-peroxidase (Sigma) at 2 µg/ml in 1x PBS, 1% BSA, 5 mM EDTA, 0.25% SDS 10–30 minutes.
(8) Wash 3×3 minutes in 2×SSC, 0.1% BSA, 0.05% Triton X-100, 1 mM EDTA, 0.25% SDS.

(9) DAB reaction: Dissolve 5 mg DAB (diaminobenzidine) in 10 ml 10 mM Tris, pH 7.5. Add 200 ul 1% CoCl$_2$ and leave on ice 10 minutes. Then add 15 ul of 30% hydrogen peroxide, and incubate with nitrocellose blot for 10 minutes - 2 hours.

Note: Buffers in Steps 7-8 are the same as those suggested by the manufacturer except for the addition of 0.25% SDS.

EXAMPLE 4

The example demonstrates the stability of the biotinylated carbodiimide DNA adduct. Carbobiotin-DNA (CB-DNA) was tested for stability at two different periods of incubation: 1) 1 hour incubation time, 30 mM borate, pH 8.5, 4 hour incubation time, 30 mM borate, pH 8.5. The stability of the modified DNA was determined by a) integrity of the modified DNA, running as a single band on a 1% agarose gel, with the DNA visualized by ethidium bromide staining, b) retention of ability to complex with streptavidin, as evidenced by color development with streptavidin-peroxidase and diamino benzidine (DAB). After removal of excess carbobiotin from the CB-DNA, its stability was tested by heating it to 37° C. or 65° C. for a designated amount of time, then running the modified DNA on an agarose gel and checking its stability by ethidium bromide staining of the gel and ability to complex with streptavidin.

No stability problems were evidenced until the CB-DNA was heated to 65° C. for 15 hours.

What is claimed is:

1. A carbodiimide compound of the Formula I:

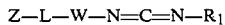

wherein Z is a biotin group; L is a divalent linking group; W is an alkylene group of up to 24 carbon atoms which can be substituted with or interrupted by a water solubility enhancing group or cleavable S—S group; R$_1$ is alkyl or substituted alkyl of up to 18 carbon atoms.

2. The compound of claim 1 wherein W is:

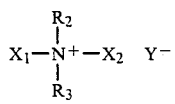

wherein X$_1$ and X$_2$ are each alkylene groups having from 1 to 18 carbon atoms, R$_2$ and R$_3$ are each alkyl groups having from 1 to 18 carbon atoms, and Y is a counterbalancing anion.

3. The compound of claim 2 having the formula:

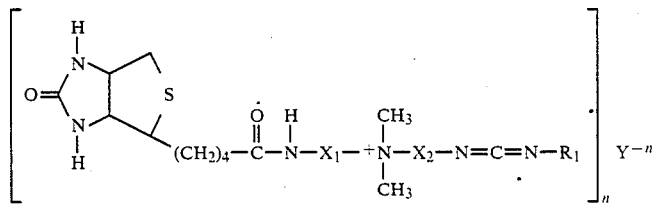

wherein X$_1$, X$_2$, R$_1$ and Y have the meanings as in claim 2 and n is an integer from 1 to 3.

4. The compound of claim 3 having the formula:

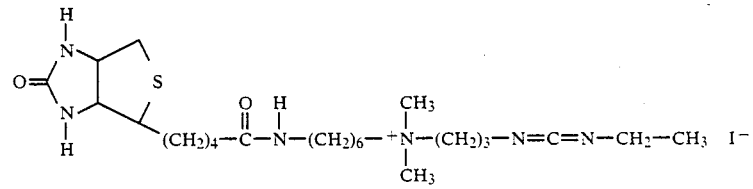

* * * * *